US012622601B2

(12) United States Patent
Chan

(10) Patent No.: US 12,622,601 B2
(45) **Date of Patent: *May 12, 2026**

(54) COMPRESSION SENSING UTILIZING SENSORS INCORPORATED IN A WEARABLE APPARATUS

(71) Applicant: Ethan Y. Chan, Fremont, CA (US)

(72) Inventor: Ethan Y. Chan, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/034,406

(22) Filed: Jan. 22, 2025

(65) Prior Publication Data

US 2025/0160680 A1      May 22, 2025

Related U.S. Application Data

(63) Continuation of application No. 18/128,968, filed on Mar. 30, 2023, now Pat. No. 12,239,431.

(51) Int. Cl.
　　*A61B 5/103*　　(2006.01)
　　*A61B 5/00*　　(2006.01)
　　*G01L 5/16*　　(2020.01)

(52) U.S. Cl.
　　CPC .......... *A61B 5/1036* (2013.01); *A61B 5/0004* (2013.01); *A61B 5/6807* (2013.01); *A61B 5/7246* (2013.01); *G01L 5/16* (2013.01); *A61B 2560/0214* (2013.01); *A61B 2562/0247* (2013.01); *A61B 2562/04* (2013.01)

(58) Field of Classification Search
　　CPC ... A61B 5/1036; A61B 5/0004; A61B 5/6807; A61B 5/7246; A61B 2560/0214; A61B 2562/0247; A61B 2562/04; A61B 2562/0219; A61B 2562/046; A61B 5/1038; A61B 5/112; A61B 5/6829; G01L 5/16; A43B 3/34
　　See application file for complete search history.

(56) References Cited

U.S. PATENT DOCUMENTS

| | | | | | |
|---|---|---|---|---|---|
| 5,148,804 | A | * | 9/1992 | Hill | A61F 7/10 607/108 |
| 5,184,613 | A | * | 2/1993 | Mintz | A61F 7/03 607/104 |
| 5,496,358 | A | * | 3/1996 | Rosenwald | A61F 7/02 607/108 |
| 2010/0211355 | A1 | * | 8/2010 | Horst | G01G 23/3735 73/172 |
| 2014/0121574 | A1 | * | 5/2014 | Chladek | A61N 1/36003 601/27 |
| 2016/0066818 | A1 | * | 3/2016 | Cowley | A61B 5/1038 600/592 |

(Continued)

*Primary Examiner* — Amine Benlagsir

(74) *Attorney, Agent, or Firm* — Vista IP Law Group, LLP

(57) ABSTRACT

An apparatus for worn by a user, includes: an elastic sleeve configured to be worn at a foot of the user; and a plurality of sensors coupled to the elastic sleeve, wherein the sensors comprise at least a first sensor configured to sense a first force or first pressure, and a second sensor configured to sense a second force or second pressure; wherein the first sensor is at a first location with respect to the elastic sleeve so that when the user wears the apparatus, the first sensor will be at a medial side of the foot; and wherein the second sensor is at a second location with respect to the elastic sleeve so that when the user wears the apparatus, the second sensor will be at a lateral side of the foot.

18 Claims, 8 Drawing Sheets

(56)                    References Cited

U.S. PATENT DOCUMENTS

| | | | |
|---|---|---|---|
| 2016/0206242 A1* | 7/2016 | Esposito | A61B 5/1038 |
| 2016/0367191 A1* | 12/2016 | Esposito | D04B 1/14 |
| 2017/0049394 A1* | 2/2017 | Zhang | A61B 5/1073 |
| 2022/0240810 A1* | 8/2022 | Huang | A61B 5/6829 |
| 2022/0257185 A1* | 8/2022 | Shen | A61B 5/6807 |
| 2022/0280101 A1* | 9/2022 | Wang | A61F 13/00051 |
| 2024/0000184 A1* | 1/2024 | Takashima | A43B 7/145 |

* cited by examiner

| Sensor value | Comfort level |
|---|---|
| 0 - 1.87 V | Comfortable |
| > 1.87 V | Uncomfortable |

1

COMPRESSION SENSING UTILIZING SENSORS INCORPORATED IN A WEARABLE APPARATUS

RELATED APPLICATION DATA

This application is a continuation of U.S. patent application Ser. No. 18/128,968 filed on Mar. 30, 2023, pending. The entire disclosure of the above application is expressly incorporated by reference herein.

FIELD

The field relates to devices and methods for determining comfort levels associated with shoe wearing, and/or for determining correct shoe sizes.

BACKGROUND

It is important to have correct footwear fitting. Footwear that is incorrectly fitted can result in foot pathology. For example, incorrect footwear fitting may cause foot pain, and foot disorders including but not limited to corns, calluses, and toe deformity.

The Brannock device is a popular instrument for determining one's shoe size. The Brannock device measures a length and a width of a person's foot, and determines the person's appropriate shoe size based on the measured dimensions. However, it is estimated that as much as 70% of the population may be wearing shoes that do not accommodate either the width or length dimensions of their feet.

More importantly, the Brannock device may not be accurate in determining the right shoe size. This is because the Brannock device merely considers the length and the width of a person's foot when determining shoe size. However, the length and the width of a person's foot only account for four potential pressure points (front tip, left most, right most, and rear tip) of the foot. Accordingly, even if the length and the width of a person's foot are considered, the person may not be wearing a correct size shoe because there may be significant pressure point(s) caused by the shoe that is not accounted for.

In addition, a person sometimes may continue to wear shoes that are slightly uncomfortable, and may bear some discomfort that comes with wearing the shoes, with the hope that the shoes will eventually be broken-in. However, in such situations, the amount of pressure exerted by the shoes towards the person's feet may be at an unhealthy level without the person realizing it, and the person may eventually develop a foot condition, such as calluses.

Also, certain individuals may not remember, or may not be able, to express discomfort at the feet when wearing shoes. For examples, children, older people, disabled individuals, and people with medical conditions (e.g., Down syndrome, diabetes, etc.) may tend to wear poorly fitted shoes more frequent than others.

Accordingly, new devices and methods for determining comfort levels associated with shoe wearing, and/or for determining correct shoe sizes for individuals are described herein.

SUMMARY

An apparatus includes: an elastic sleeve configured to be worn at a foot of a user; and a plurality of sensors coupled to the elastic sleeve, wherein the sensors comprise at least a first sensor configured to sense a first force or first pressure, and a second sensor configured to sense a second force or second pressure; wherein the first sensor is at a first location with respect to the elastic sleeve so that when the user wears the apparatus, the first sensor will be at a medial side of the foot; and wherein the second sensor is at a second location with respect to the elastic sleeve so that when the user wears the apparatus, the second sensor will be at a lateral side of the foot.

Optionally, the elastic sleeve comprises a first layer and a second layer, and wherein the sensors are disposed between the first layer and the second layer of the elastic sleeve.

Optionally, the sensors comprise an array of sensors that includes the first and second sensors.

Optionally, the elastic sleeve and the sensors form a wearable device, and wherein the wearable device comprises one or more transmitters configured to transmit sensor data from the sensors to a device away from the wearable device.

Optionally, the device comprises a cellular phone, an iPad, a tablet, a computer, a sport-band, a watch, or a server.

Optionally, the apparatus further includes a battery compartment configured to house a battery, wherein the sensors are configured to operate utilizing power from the battery.

Optionally, the apparatus further includes an energy harvester configured to obtain energy from motion of the user.

Optionally, the apparatus further includes a switch coupled to the sensors, wherein the switch is manually operable to turn the sensors on or off.

Optionally, the elastic sleeve is washable and re-usable.

Optionally, the sensors comprise a third sensor configured to sense a third force or third pressure applied by a bottom of the foot of the user.

Optionally, the apparatus further includes an array of sensors, the array of sensors located with respect to the elastic sleeve so that when the user wears the apparatus, the array of sensors will be at a bottom of the foot.

Optionally, at least a part of the array of sensors is located with respect to the elastic sleeve so that when the user wears the apparatus, the at least the part of the array of sensors is below a metatarsal head of the foot, a tibial sesamoid of the foot, a fibular sesamoid of the foot, a great toe of the foot, a plantar medial tubercle of the foot, a calcaneal-cuboid joint of the foot, a 5th metatarsal base of the foot, or any combination of the foregoing.

Optionally, the apparatus further includes one or more registers or one or more memories configured to store sensor data from the sensors, wherein the one or more registers or the one or more memories are secured to the elastic sleeve.

Optionally, the sensors are secured to the elastic sleeve via respective adhesive and/or respective stitching fibers.

Optionally, the apparatus further includes one or more displays configured to display information derived from sensor data provided by the sensors.

Optionally, the apparatus is configured to provide sensor data from the sensors in a data structure that correlates the sensor data with respective time points.

Optionally, the sensors also comprise a third sensor at a third location with respect to the elastic sleeve so that when the user wears the apparatus, the third sensor will be at a bottom of the foot distal to a lisfrank's joint.

Optionally, the sensors also comprise a fourth sensor at a fourth location with respect to the elastic sleeve so that when the user wears the apparatus, the fourth sensor will be at the bottom of the foot proximal to the chopart's joint.

Optionally, the apparatus further includes a mapping table mapping a first range of sensor values to a comfort classification, and mapping a second range of sensor values to a discomfort classification.

Optionally, the apparatus further includes a visual indicator configured to provide a visual indication when a sensor value associated with the first sensor or the second sensor is below a threshold.

Optionally, the apparatus further includes a visual indicator configured to provide a visual indication when a sensor value associated with the first sensor or the second sensor is above a threshold.

An apparatus includes: an elastic sleeve configured to be worn at a foot of a user; and a plurality of sensors coupled to the elastic sleeve, wherein the sensors comprise at least a first sensor configured to sense a first force or first pressure, and a second sensor configured to sense a second force or second pressure; wherein the first sensor is at a first location with respect to the elastic sleeve so that when the user wears the apparatus, the first sensor will be away from a bottom of the foot; and/or wherein the second sensor is at a second location with respect to the elastic sleeve so that when the user wears the apparatus, the second sensor will be away from the bottom of the foot.

Other and further aspects and features will be evident from reading the following detailed description.

BRIEF DESCRIPTION OF THE DRAWINGS

The drawings illustrate the design and utility of embodiments, in which similar elements are referred to by common reference numerals. In order to better appreciate how advantages and objects are obtained, a more particular description of the embodiments will be described with reference to the accompanying drawings. Understanding that these drawings depict only exemplary embodiments and are not therefore to be considered limiting in the scope of the claimed invention.

FIGS. 11A-11E illustrate variations of the wearable device of FIG. 1, particularly showing different sensor arrangements for sensing forces/pressures at different sides of a foot.

FIGS. 12A-11D illustrate variations of the wearable device of FIG. 1, particularly showing the wearable device further include sensors at a bottom of an elastic sleeve.

DESCRIPTION OF THE EMBODIMENTS

Figure 1:
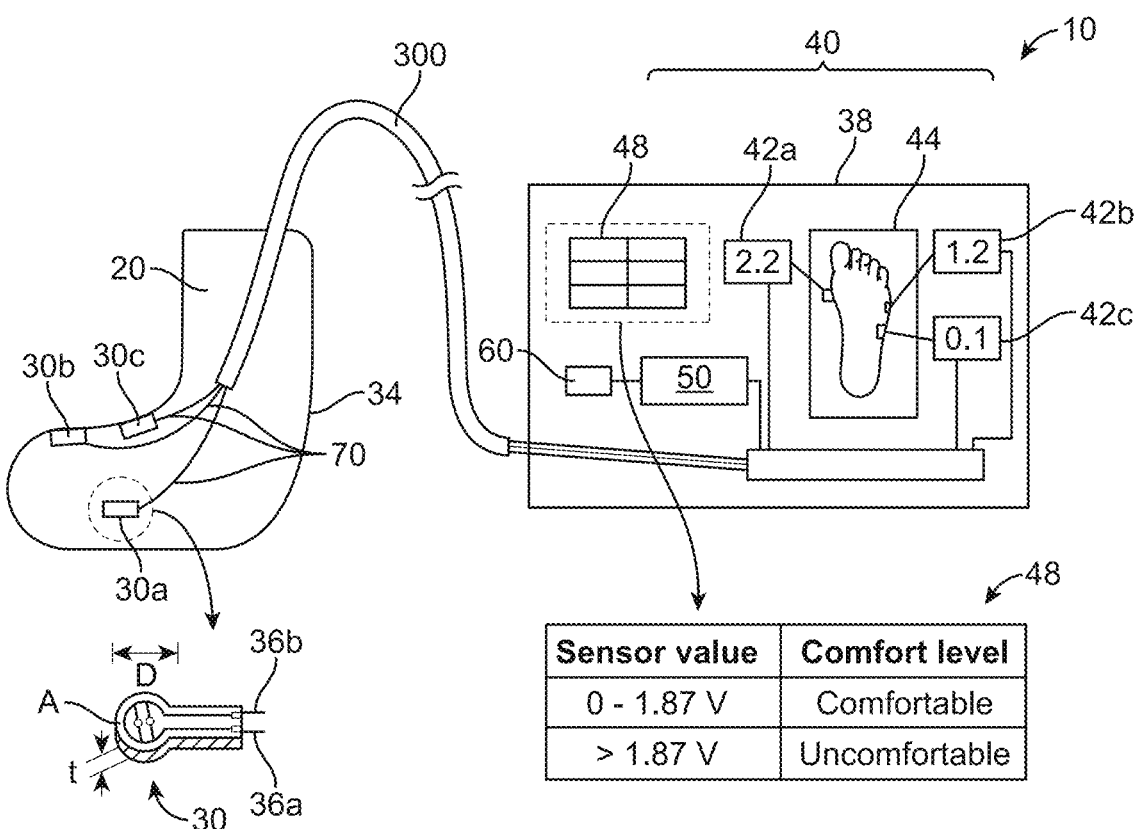
FIG. 1 illustrates an apparatus that includes a wearable device and a user interface device in accordance with some embodiments.

Various embodiments are described hereinafter with reference to the figures. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages of the invention shown. An aspect or an advantage described in conjunction with a particular embodiment is not necessarily limited to that embodiment and can be practiced in any other embodiments even if not so illustrated or if not so explicitly described.

FIG. 1 illustrates an apparatus 10 in accordance with some embodiments. The apparatus 10 is for worn by a user. The apparatus 10 includes an elastic sleeve 20 configured to be worn at a foot of the user; and a plurality of sensors 30 coupled to the elastic sleeve 20, wherein the sensors 30 comprise at least a first sensor 30a configured to sense a first force or first pressure, and a second sensor 30b configured to sense a second force or second pressure. The first sensor 30a is at a first location with respect to the elastic sleeve 20 so that when the user wears the apparatus 10, the first sensor 30a will be at a medial side of the foot. The second sensor 30b is at a second location with respect to the elastic sleeve 20 so that when the user wears the apparatus 10, the second sensor 30b will be at a lateral side of the foot (e.g., towards the front of the foot).

The apparatus 10 also optionally includes a third sensor 30c coupled to the elastic sleeve 20. The third sensor 30c is at a third location with respect to the elastic sleeve 20 so that when the user wears the apparatus 10, the third sensor 30c will be at a lateral side at the middle of the foot.

The elastic sleeve 20 together with the sensors 30 form a wearable device 34. In the illustrated embodiments, the wearable device 34 (comprising the elastic sleeve 20 and the sensors 30) has a form-factor of a sock configured to be worn by a foot of the user.

In the illustrated embodiments, the elastic sleeve 20 comprises a single layer, and the sensors 30 are disposed at the exterior surface of the layer. In other embodiments, the elastic sleeve 20 may optionally further include an additional layer. In such cases, the additional layer (second layer) may be disposed over the first layer so that the sensors 30 are located (sandwiched) between the first and second layers of the elastic sleeve 20. The second layer of the elastic sleeve 20 is advantageous because it protects the sensors 30 from wear and tear, and may prevent the sensors 30 from being pulled away and detached from the first layer (during insertion of the elastic sleeve 20 into a shoe, and/or during removal of the elastic sleeve 20 from the shoe). In further embodiments, the elastic sleeve 20 may include more than two layers. For example, in further embodiments, the elastic sleeve 20 may include three layers, four layers, etc. In some cases, the third layer may be disposed inside the first layer, and may be detachably secured to the first layer via a connector (e.g., Velcro, adhesive, snap button, zipper, etc.), or via friction. The third layer may be a hygiene-layer that is disposable after each use. The hygiene-layer separates the user's foot from the first layer, and prevents the user's foot from making contact with the first layer. In some cases, multiple hygiene-layers (third layers) may be provided, and the user may replace each of the hygiene-layers after each use.

In some embodiments, the elastic sleeve 20 is washable and re-usable. In other embodiments, the elastic sleeve 20 may be configured for a single-use, or a limited number of uses.

In some cases, the sensors 30 may be secured to the elastic sleeve 20 via respective adhesive, respective tapes, respective stitching fibers, or any combination of the foregoing.

In the illustrated embodiments, each sensor 30 is a pressure sensor configured to sense pressure. In other embodiments, each sensor 30 may be a force sensor configured to sense force. In further embodiments, each sensor 30 may be configured to sense a characteristics associated with a force/pressure applied towards the sensor 30.

Referring to FIG. 1, each sensor 30 has a first sensor terminal 36*a*, and a second sensor terminal 36*b*. The sensor terminals 36*a*, 36*b* are configured to electrically coupled (directly or indirectly) to a power source (e.g., to respective battery terminals of a battery).

The sensor 30 may have a thickness t that is less than 1 mm, or more preferably less than 0.6 mm, less than 0.5 mm, less than 0.4 mm, less than 0.3 mm, or less than 0.2 mm. Having a thin sensor 30 is desirable because it will not interfere with how the user's shoe interacts with the user's foot while the user is wearing the wearable device 34.

In some cases, each sensor 30 may have a weight that is less than 5 g, or more preferably less than 4 g, less than 3 g, less than 2 g, or less than 1 g. Having a light weight sensor 30 is desirable because it will not require the user to exert significant effort to carry the sensor 30 while wearing the wearable device 34.

In some cases, each sensor 30 may be a pressure sensor implemented using a strain gauge, a piezoelectric component, a capacitive sensing component, a resistor, etc. In other cases, each sensor 30 may be a force sensor. The force sensor may be implemented using load cell (e.g., pneumatic load cell, hydraulic load cell, piezoelectric crystal load cell, inductive load cell, capacitive load cell, magnetostrictive load cell, strain gauge load cell, etc.), strain gauge, force sensing resistor, etc.

As shown in FIG. 1, in some cases, each sensor 30 may have a sensing area A with a maximum cross-sectional dimension D that is 12 mm or less, or more preferably less than 10 mm, less than 9 mm (e.g., 8 mm), less than 8 mm, less than 6 mm, or less than 4 mm. The sensing area may have a circular shape, an elliptical shape, a square shape, or any of other geometric shapes. In other cases, each sensor 30 may have a sensing area with a maximum cross-sectional dimension that is more than 12 mm.

In some embodiments, each sensor 30 is configured to generate a voltage within a range of 0V to 3V in response to force or pressure applied to the sensor 30 while the user is wearing the apparatus 10 with a shoe. The force or pressure is due to a part of the shoe pressing towards the sensor 30. In other embodiments, the voltage provided by each sensor 30 may have a range that is different from that described above. For example, the voltage range may have an upper limit that is more or less than 3V, and/or a lower limit that is higher or lower than 0V.

Also, in some embodiments, each sensor 30 is configured to generate a voltage in response to a force that is within a range of 0N to 300N. In other embodiments, the upper limit of the sensed force may be more than 300N or less than 300N. For example, in other embodiments, the upper limit of the sensed force may be 200N, 100N, 80N, 70N, 60N, 50N, 40N, 30N, or 20N.

In some cases, the output of each sensor 30 may be proportional to the sensed force/pressure. In such cases, the sensed characteristic (force/pressure) by the sensor 30, and the output of the sensor 30, form a linear relationship. In other cases, the output of each sensor 30 may be non-proportional to the sensed force/pressure. In such cases, the sensed characteristic (force/pressure) by the sensor 30, and the output of the sensor 30, form a non-linear relationship. For example, the non-linear relationship may be a logarithmic relationship, or any of other non-linear relationships.

It should be noted that each sensor 30 should not be limited to the examples described, and that each sensor 30 may have other configurations in other embodiments. For example, in other embodiments, each sensor 30 may have a size and/or a shape that is different from the examples described. Also, in other embodiments, at least a part of the sensor 30, or an entirety of the sensor 30 may be integrated with the elastic sleeve 20. For example, in some embodiments, the elastic sleeve 20 may be a sock made from a fabric, and component(s) of the sensor 30 may be integrated with the fabric. In one implementation, component(s) (e.g., conductor) of the sensor 30 may be weaved with fibers of the fabric.

As shown in FIG. 1, the apparatus 10 further includes a battery holder 50 configured to house a battery, wherein the sensors 30 and the displays 42 are configured to operate utilizing power from the battery. Alternatively or additionally, the apparatus 10 may include an energy harvester configured to obtain energy from motion of the user. The energy harvester may utilize piezoelectric, electromagnetic, and triboelectric energy harvesting technologies from human motions, such as limb swing, joint rotation, force application, etc.

The apparatus 10 may optionally further include a switch 60 coupled to the sensors 30, wherein the switch 60 is manually operable to turn the sensors 30 and the displays 42 on or off.

As shown in FIG. 1, the apparatus 10 also includes a user interface device 38 providing a user interface 40. The user interface 40 is configured to provide information to the user of the apparatus 10. The user interface 40 includes three displays 42*a*-42*c* configured to display information based on outputs from the respective sensors 30*a*-30*c*. The user interface 40 optionally further includes a foot-diagram 44 indicating the pressure sensing areas with respect to a user's foot that correspond with the respective displays 42*a*-42*c*. In the illustrated embodiments, the display 42*a* is configured to provide information indicating sensed force/pressure at the medial side of the user's foot, and the display 42*b* is configured to provide information indicating sensed force/pressure at the lateral side of the user's foot at a location that is closer to the front of the foot. The display 42*c* is configured to provide information indicating sensed force/pressure at the lateral side of the user's foot at a location that is closer to the middle of the foot.

In the illustrated embodiments, the foot-diagram 44 is a physical object—e.g., a printed diagram. Alternatively, the foot-diagram 44 may be a graphical object displayed by a screen. In such cases, the foot-diagram 44 may be stored in a non-transitory medium, and the user interface device 38 may include a screen for displaying the foot-diagram 44.

Each display 42 is configured to display information derived from output (sensor data) from the corresponding sensor 30. In some embodiments, each display 42 may be configured to display voltage value representing an amount of voltage output by the corresponding sensor 30. In other embodiments, each display 42 may be configured to display force value, or pressure value, that corresponds with the output from the corresponding sensor 30. In further embodiments, each display 42 may be configured to display a metric indicating or correlating with an amount of force or pressure sensed by the corresponding sensor 30. Also, in some embodiments, each display may be configured to provide a visual indicator (e.g., a color, a "high"/"low" message, etc.) indicating whether a sensed force or pressure is too high. In some embodiments, two or more of the above visual information may be displayed by each display 42. Thus, each display 42 may be configured to display one or more visual information described above.

In some embodiments, each display 42 may be configured to display information based on output from the sensor 30. For example, if output from the sensor 30 is a voltage, the display 42 may be configured to receive the voltage, and display a voltage value indicating an amount of the received voltage. In such cases, there may be no need to have any processing unit to process the output from the sensor 30. However, in other embodiments, the apparatus 10 may optionally further include a processing unit (e.g., processing unit 710 at the wearable device 34 described below, or a processing unit at the user interface device 38) configured to process outputs from the sensors 30, and to provide a processed output for receipt by the display 42. The display 42 then displays the processed output from the processing unit. In some embodiments, the processing unit may be configured to calculate the processed output based on the sensor output. For example, the calculation may be based on a formula that relates voltage value from the sensor 30 with force/pressure. In other embodiments, the processing unit may be configured to access a lookup table (that maps sensor outputs to respective metric values, such as force values/pressure values), and provide a looked-up metric as the processed output. The metric values may be force values, pressure values, comfort levels, etc., or any of other metric values. In some cases, the lookup table may map voltage values from the sensors 30 to respective force/pressure values. In other cases, the lookup table may map voltage values from the sensors 30 to respective comfort levels. In further cases, if the sensor outputs are force/pressure values, the lookup table may map force/pressure values with respective comfort levels. As a further example, the processing unit may be configured to reformat the sensor output, and/or to package the sensor output, and provide the reformatted and/or packaged output as the processed output. By means of non-limiting examples, the processing unit may be a processor, software, a combination of software and hardware, one or more hardware components, a hardware and/or a software component implementing a mathematical operator, etc. In some cases, the processing unit may be configured to output respective processed output (based on processing of respective sensor outputs from the respective sensors 30) to the respective displays 42. In such cases, the processing unit may be, or may include, a multiplexer (MUX) configured to receive sensor outputs from the sensors 30, and output processed signals to corresponding displays 42. It should be noted that the signals output by the processing unit may be the sensor outputs themselves, or may be metric values that are different from the sensor outputs. Thus, as used in this specification, the term "processed signal", "information derived from sensor data", or any of other similar terms, may refer to information/data/ signal that is the same as the sensor output from the sensor 30, or may refer to information/data/signal that is different from the sensor output.

As shown in FIG. 1, the user interface 40 further includes a comfort-level chart 48 configured to correlate information displayed by the sensor 42a/42b/42c with comfort levels. In some embodiments, the comfort-level chart 48 may include at least two ranges of metric values, wherein the first metric value range corresponds with "comfortable" (comfort) classification, and the second metric value range corresponds with "uncomfortable" (discomfort) classification. In other embodiments, the comfort-level chart 48 may include more than two classifications. For example, the comfort-level chart 48 may include three comfort level classifications (such as comfort levels 1, 2, 3). As another example, the comfort-level chart 48 may include three ranges of metric values corresponding with three shoe-fitting classifications, wherein the first metric value range corresponds with "too loose" classification (indicating shoe is too loose), the second metric value range corresponds with "right fit" classification (indicating shoe is the right fit), and the third metric value range corresponds with "too tight" classification (indicating shoe is too tight).

Various techniques may be employed to create the comfort-level chart 48. In one implementation, during a statistical sampling process, one or more persons may be asked to wear shoes of different sizes, brands, types, models, etc., while also wearing the wearable device 34. The values displayed by the displays 42, and the person's subject feelings (e.g., comfort levels) for the corresponding values, may be recorded. After the data collection has been completed, there will be a list of values (obtained using the sensors 30) and their corresponding comfort levels felt subjectively by the person(s). In some cases, the comfort levels felt subjectively by the person(s) may include two groups-"comfortable" and "uncomfortable". In such cases, all of the values associated with "comfortable" may be combined to form a first range of values (sensor-based values) representing the "comfortable" classification, and all of the values associated with "uncomfortable" may be combined to form a second range of values (sensor-based values) representing "uncomfortable" classification.

In the illustrated embodiments, the comfort-level chart 48 is a physical object—e.g., a printed diagram. Alternatively, the comfort-level chart 48 may be a graphical object displayed by a screen. In such cases, the comfort-level chart 48 may be stored in a non-transitory medium, and the user interface device 38 may include a screen for displaying the comfort-level chart 48.

As shown in the figure, the displays 42, the foot diagram 44, the comfort-level chart 48, the battery holder 50, and the switch 60 are implemented as parts of the user interface device 38. In other embodiments, the battery holder 50, the switch 60, the displays 42, the foot diagram 44, the comfort-level chart 48, or any combination of the foregoing, may be coupled to the elastic sleeve 20 so that one or more of these components are parts of the wearable device 34.

In other embodiments, instead of the multiple displays 42, the user interface 40 may include a single screen configured to provide information indicating sensed forces/pressures at different areas based on outputs from the sensors 30. The screen may also display the foot diagram 44 and/or the comfort-level chart 48.

Also, in some embodiments, the apparatus 10 may optionally include an output generator configured to provide a visual and/or audio output informing the user or a caregiver about a comfort level of a shoe being worn by the user. For example, the apparatus 10 may include a processing unit (such as the processing unit 710 described herein) implemented at the wearable device 34 and/or the user interface device 38. The processing unit is configured to determine whether a sensor output from the sensor 30 satisfies one or more criteria, and if so, the processing unit will generate a control signal to cause the output generator to provide the visual and/or audio output. For example, in some embodiments, the processing unit may be configured determine whether a sensor value (or a value derived therefrom) associated with the first sensor 30a or the second sensor 30b is below a threshold, and may generate the control signal if the sensor value or the derived value is below the threshold. As another example, in other embodiments, the processing unit may be configured determine whether a sensor value (or a value derived therefrom) associated with the first sensor 30a or the second sensor 30b is above a threshold, and may generate the control signal if the sensor value or the derived value is above the threshold. In some embodiments, the output generator may be a speaker configured to provide sound as the audio output. For example, the speaker may provide a first audio output (e.g., first beep with first pitch, first audio message, etc.) indicating comfort when the sensor value or the derived value is below a threshold, and may provide a second audio output (e.g., second beep with second pitch, second audio message, etc.) indicating discomfort when the sensor value or the derived value is above the threshold or another higher threshold (indicating discomfort). In other embodiments, the output generator may be a LED configured to provide light as the visual output, or may be a screen configured to display visual information as the visual output. For example, a LED may provide a green light if the processing unit determines that the sensor value or the derived value is below a threshold (indicating comfort), and a LED may provide a red light if the processing unit determines that the sensor value or the derived value is above the threshold or above another higher threshold (indicating discomfort). In some embodiments, in which the user interface device 38 includes a single screen (instead of the displays 42), the screen may be configured to provide the visual output. For example, the screen may display a first graphic (e.g., first object, first text, etc.) if the processing unit determines that the sensor value or the derived value is below a threshold (indicating comfort), and may display a second graphic if the processing unit determines that the sensor value or the derived value is above the threshold or above another higher threshold (indicating discomfort). In further embodiments, the output generator may include both the speaker and the LED/screen, for providing both audio and visual output.

Figure 2:
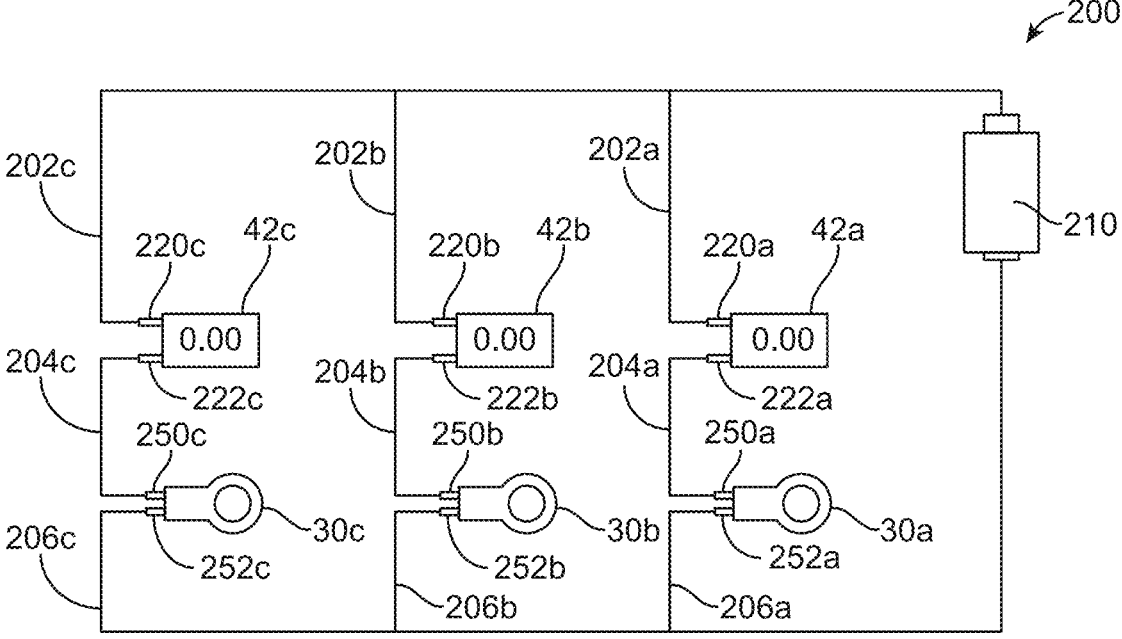
FIG. 2 illustrates a circuit diagram of the apparatus of FIG. 1.

FIG. 2 illustrates an electrical diagram representing the circuit 200 of the apparatus 10 of FIG. 1. As shown in the figure, the circuit 200 includes the sensors 30a-30c, and the three corresponding displays 42a-42c. The circuit 200 also includes a power source (e.g., battery) 210 for supplying power for the sensors 30a-30c and the displays 42a-42c. The displays 30a-30c are coupled to one of the two terminals of the power source 210 in parallel via respective conductors 202a-202c. Also, the sensors 30a-30c are coupled in series with respect to corresponding displays 42a-42c via respective conductors 204a-204c, and are coupled in parallel to one of the two terminals of the power source 210 via conductors 206a-206c. In the illustrated embodiments, each display 42 has a first display terminal 220 (e.g., terminal 220a/220b/220c) and a second display terminal 222, wherein the first display terminal 220 is connected to the power source 210 via the conductor 202 (e.g., conductor

202a/202b/202c). Each sensor 30 has a first sensor terminal 250 and a second sensor terminal 252. The second display terminal 222 (e.g., terminal 222a/222b/222c) of each display 42 is coupled to the first sensor terminal 250 of the corresponding sensor 30 via the conductor 204 (e.g., conductor 204a/204b/204c). The second sensor terminal 252 of the sensor 30 is coupled to the power source 210 via the conductor 206 (e.g., conductor 206a/206b/206c).

The apparatus 10 may include fewer than three sensors 30 (e.g., two sensors 30) and fewer than three displays 42 (e.g., two displays 42). In such cases, the circuit 200 of the apparatus 10 will include fewer than three sensors 30 and fewer than three displays 42. In other embodiments, the circuit 200 may include more than three sensors 30 and more than three displays 42.

During use, the power source 210 provides power for the sensors 30a-30c and the displays 42a-42c. Each sensor 30 provides a voltage that corresponds with an amount of force/pressure sensed by the sensor 30. In some embodiments in which each sensor 30 has a resistor that changes resistance in response to the sensed force/pressure, the voltage outputted by the sensor 30 will change accordingly. Each display 42 is configured to receive a corresponding voltage from the corresponding sensor 30, and display a voltage value of the received voltage. Thus, as each sensor 30 outputs a voltage that is variable based on the sensed force/pressure, the voltage value displayed by the corresponding display 42 will change accordingly.

Figures 3, 4:
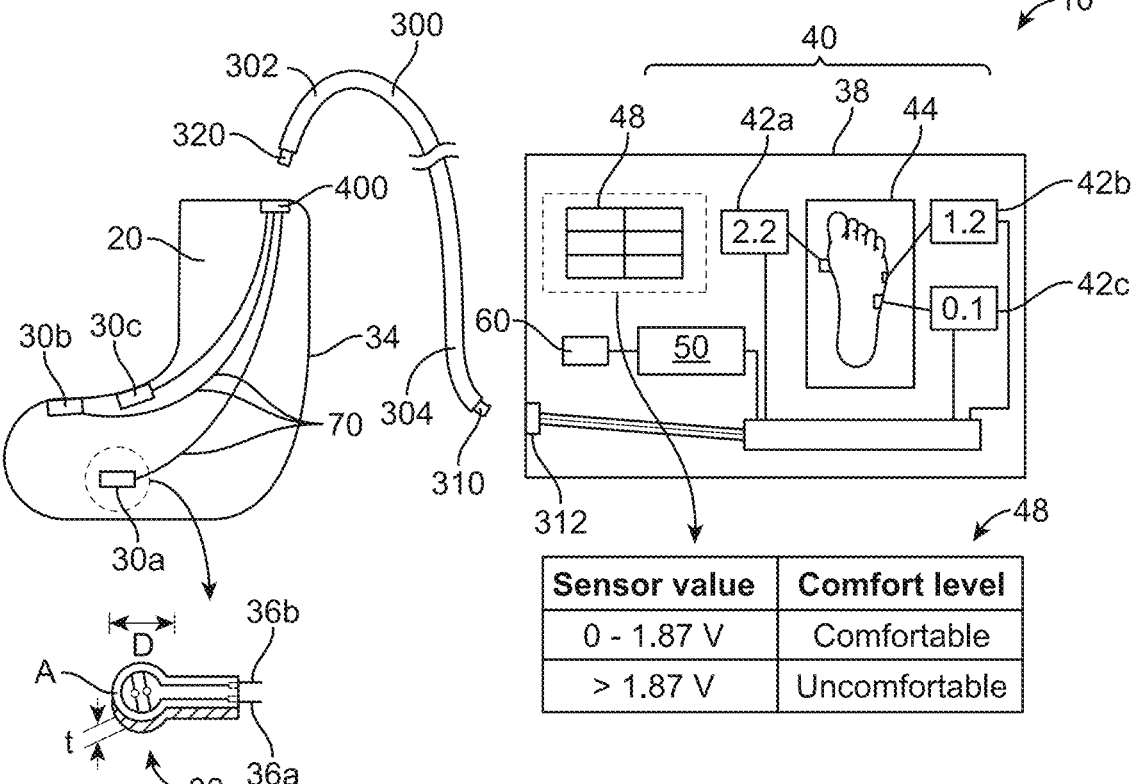
FIG. 3 illustrates a variation of the apparatus of FIG. 1.
FIG. 4 illustrates another variation of the apparatus of FIG. 1.

In the illustrated embodiments, the sensors 30 at the elastic sleeve 20 are electrically connected to the user interface device 38 via respective wires 70. The wires 70 may be "hardwired" to both the sensors 30 and to the user interface device 38. In other embodiments, the sensors 30 at the wearable device 34 may be electrically coupled to the user interface device 38 via a cable 300 (FIG. 3). The cable 300 may have wires 70 "hardwired" to the sensors 30 at first ends 302 of the respective wires 70. The second ends 302 of the respective wires 70 may be electrically connected to a connector 310 at an end of the cable 300. The connector 310 is configured to electrically and detachably connected to the user interface device 38 at a corresponding connector 312 at the user interface device 38. The user interface device 38 of FIG. 3 is the same as that of FIG. 1, and therefore, it will not be described again.

In further embodiments, as shown in FIG. 4, the wearable device 34 may be detachably coupled to the user interface device 38 via a cable 300 containing the wires 70, wherein the first ends 302 of the respective wires 70 are connected to a first connector 320, and the second ends 304 of the respective wires 70 are connected to the second connector 310. The first and second connectors 320, 310 are on opposite ends of the cable 300. The first connector 320 may be detachably connected to the wearable device 34 at a corresponding connector 400 at the wearable device 34. The second connector 310 may be detachably connected to the user interface device 38 at the corresponding connector 310 at the user interface device 38. The user interface device 38 of FIG. 4 is the same as that of FIG. 1, and therefore, it will not be described again.

During use of the apparatus 10, the user wears the wearable device 34 at the foot by slipping the elastic sleeve 20 over the foot. After the elastic sleeve 20 is placed over the foot, the first sensor 30a is at a medial side of the foot (above/away from the bottom of the foot), and the second sensor 30b and the third sensor 30c are at a lateral side of the foot (above/away from the bottom of the foot). The switch 60 is then turned on to provide power for the sensors 30c and the displays 42a-42c Next, the user insert the foot (with the wearable device 34) into a shoe. In response to force or pressure applied at the areas of the sensors 30a-30c by the shoe, the sensors 30a-30c will generate respective voltages that are associated with (e.g., that indicate or represent) the respective sensed forces or sensed pressures.

In the illustrated example, the displays 42a-42c are configured to display the respective voltages provided respectively by the sensors 30a-30c. The display 42a displays a voltage of "2.2" volts, the display 42b displays a voltage of "1.2" volts, and the display 42c displays a voltage of "0.1" volt. The foot diagram 44 indicates the locations of the foot for which the displays 42a-42c provide the voltage values. The user, or a caregiver of the user, can view the foot diagram 44 together with the displays 42a-42c, and can determine that the 2.2 V value is for the medial side of the foot, the 1.2 V value is for the lateral side at the front of the foot, and the 0.1 V value is for the lateral side at the middle of the foot. The comfort-level chart 48 at the user interface device provides the below mapping information:

| Sensor data | Comfort level |
| --- | --- |
| 0-1.87 V | Comfortable |
| >1.87 V | Uncomfortable |

Thus, the user, or the caregiver of the user can use the comfort-level chart 48 to determine that the medial side of the user foot is uncomfortable (because the sensor value of 2.2 V falls within the range ">1.87V" which is mapped by the comfort-level chart as "Uncomfortable". Similarly, it can be determined that the lateral side at the front of the user foot is comfortable (because the sensor value of 1.2 V falls within the range "0-1.87V" which is mapped by the comfort-level chart as "Comfortable". Also, it can be determined that the lateral side at the middle part of the user foot is comfortable (because the sensor value of 0.1 V falls within the range "0-1.87V" which is mapped by the comfort-level chart as "Comfortable".

Figure 5:
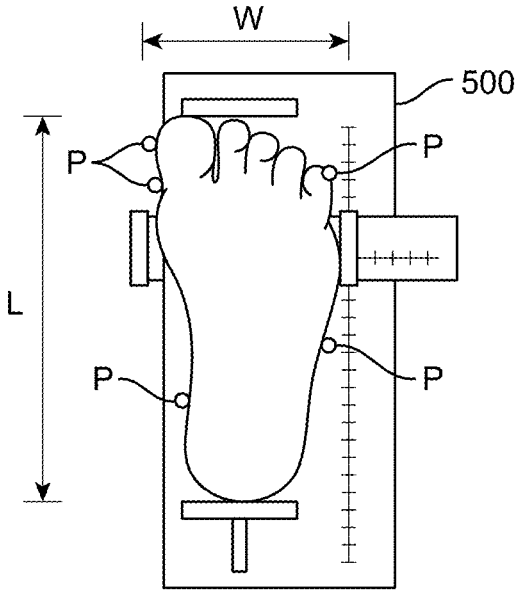
FIG. 5 illustrates a Brannock device.

As shown in the above example, the apparatus 10 is beneficial in assisting the user, or a caregiver of the user, to determine whether a shoe being worn by the user is comfortable or not. In some cases, the user may bring the apparatus 10 when purchasing a new pair of shoes, and can use the apparatus 10 to determine whether a size of the new pair of shoes is the correct size for the user or not. The apparatus 10 is advantageous over the Brannock device 500 because the Brannock device 500 merely measures a length L and a width W of a person's foot, and determines the person's shoe size based on only these two measured dimensions (see FIG. 5). The technique utilized by the Brannock device 500 is not accurate in determining the appropriate shoe size because potential pressure points P at the person's foot may not be detectable by the Brannock device 500. On the other hand, the sensors 30 at the wearable device 34 can provide outputs indicating pressure points P at the person's foot that are otherwise not accounted for by the Brannock device 500.

The apparatus 10 is also advantageous because a caregiver may use the apparatus 10 to determine whether there is any discomfort at a foot of a person, who may not remember, or may not be able, to express his/her discomfort. For example, a child, an elderly, a disabled person, or a person with a medical condition, may not remember or may not be able to express discomfort at the foot when wearing a shoe. However, utilizing the apparatus 10, a caregiver may determine whether the person has any discomfort when wearing a shoe. The sensors 30 samples the force/pressure at different parts of the person's foot, and the comfort-level chart 48 of the apparatus 10 objectively informs the caregiver the comfort levels at the different part of the person's foot.

In some cases, the comfort-level chart 48 may be based on data collected from a population of individuals (e.g., at least 2, and more preferably more than 2, such as 4, 5, 6, 7, 8, 9, 10, 20, 30, 40, 50, 60, 70, or more than 70 individuals). In such cases, the comfort levels in the comfort-level chart 48 may be considered as "objective" comfort levels (i.e., it is "objective" because it is based on a certain size of population). Such objective comfort levels are established comfort levels based on sensor data, and may be used objectively to determine comfort level for a user. Using objective comfort level in lieu of a person's subjective feeling to determine comfort level is advantageous. This is because a person sometimes may continue to wear shoes that are slightly uncomfortable, and may bear some discomfort that comes with wearing the shoes. In such situations, the amount of pressure exerted by the shoes towards the person's feet may be at an unhealthy level without the person realizing it, and the person may eventually develop a foot condition, such as calluses. The comfort-level chart 48 solves this problem because it may be used to objectively determine the comfort level of the user based on sensor data collected from the sensors 30 at the wearable device 34 being worn by the user. As such, even if the user may not feel or express significant discomfort, if the comfort-level chart 48 indicates that the sensor value is in a range that constitutes as "uncomfortable" objectively, that means the user may require better fitted shoes.

In the above embodiments, the apparatus 10 is described as having both the wearable device 34 and the user interface device 38. It should be noted that the apparatus 10 may include the wearable device 34, and not the user interface device 38 in other embodiments. In further embodiments, the apparatus 10 may include the user interface device 38, and not the wearable device 34.

In the above embodiments, the apparatus 10 is described as having the user interface device 38. In some cases, the user interface device 38 may be a desktop device configured for placement at a table. Alternatively, the user interface device 38 may be a handheld device configured to be held by the user or a caregiver. In such cases, the user interface device 38 may optionally include a handle. In other cases, the user interface device 38 may be a wristband for worn by the user. Thus, the user interface device 38 may optionally include a wristband or a wrist-strap.

Figure 6:
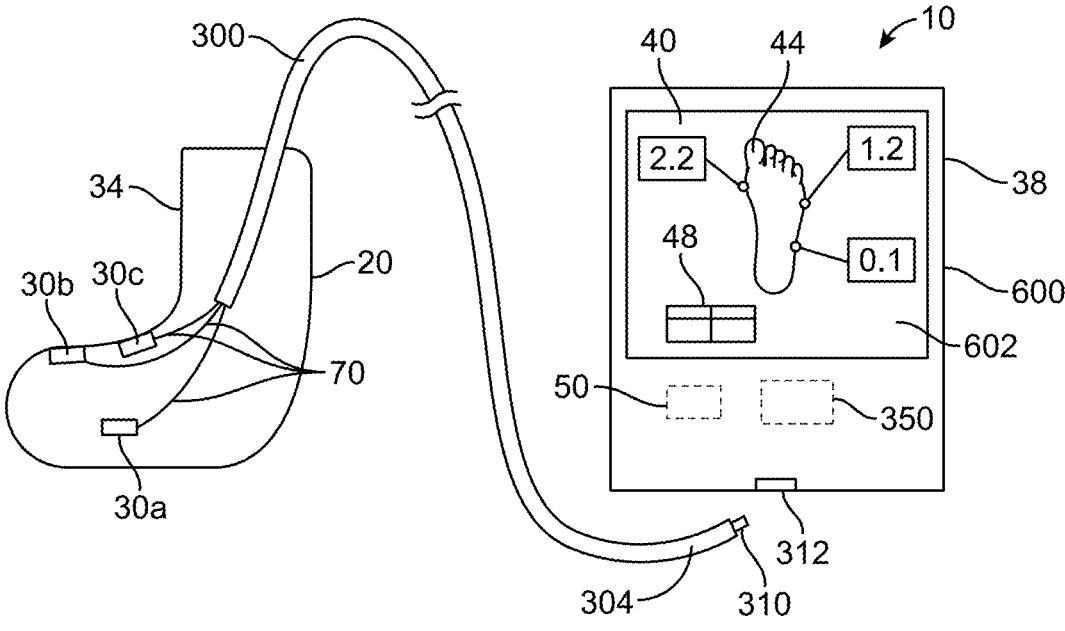
FIG. 6 illustrates another variation of the apparatus of FIG. 1.

In further embodiments, the user interface device 38 may be a phone 600, such as a smart phone or a cell phone (FIG. 6). The apparatus 10 of FIG. 6 is the same as that of FIG. 3, except that the user interface device 38 is a cell phone 600, which includes a processing unit 350. In such cases, the apparatus 10 may include the cable 300 extending from wearable device 34 like that discussed with reference to FIG. 3. The cable 300 has the connector 310 at one end of the cable 300. The connector 310 may be configured to couple with the charging port and/or the input port 312 of the phone 600. Also, in some cases, the cable 300 may have two connectors 310, 320 at opposite ends of the cable 300, for detachably coupling with the phone 600 and the wearable device 34, respectively, as similarly discussed with reference to FIG. 4. In the embodiments of FIG. 6, the user interface 40 may be implemented by the screen 602 of the phone 600. For example, the information displayed by the displays 42*a*-42*c* discussed previously may instead be displayed by the screen 602 of the phone 600. Similarly, the foot diagram 44 and the comfort-level chart 48 may also be displayed by the screen 602 of the phone 600. In the illustrated embodiments, the battery holder 50 is implemented as a compartment inside the phone 600, and the switch 60 may be implemented as the on-off switch of the phone 600, or as a selectable object displayed by the screen 602 of the phone 600.

In the above embodiments, the apparatus 10 has been described as having a cable 300 containing wires 70 that are configured to deliver signals from the sensors 30*a*-30*c* to the user interface device 38. In other embodiments, the wearable device 34 of the apparatus 10 may include a wireless device configured to wirelessly transmit signals from the sensors 30*a*-30*c* for reception by the user interface device 38 (e.g., any of the user interface devices described with reference to FIGS. 1, 3, 4, 6).

Figure 7:
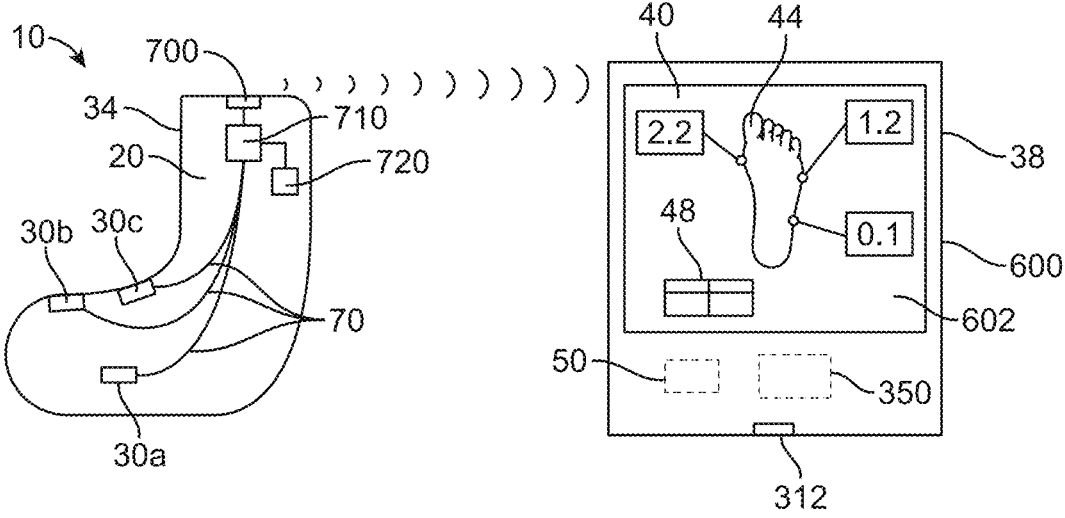
FIG. 7 illustrates another variation of the apparatus of FIG. 1.

For example, as shown in FIG. 7, the wearable device 34 of the apparatus 10 may include a wireless device 700 configured to wirelessly transmit signals from the sensors 30*a*-30*c* for reception by an iPhone 600 (as an example of the user interface device 38). The wireless device 700 may be a wireless transmitter or a wireless transceiver. The wireless device 700 may include an antenna configured to communicate with the phone 600 via short-range technology, such as Bluetooth signals, ultrasound signals, infrared signals, electromagnetic signals, etc. The wearable device 34 may also include a processing unit 710 configured to process sensor signals from the sensors 30*a*-30*c*, before passing them for wireless transmission by the wireless device 700. As shown in the figure, the wearable device 34 may also include a power source 720 configured to provide power for the processing unit 710 and the wireless device 700. The power source 720 may be a battery (e.g., a rechargeable battery), or may be an energy harvester configured to obtain energy from motion of the user.

Figure 8:
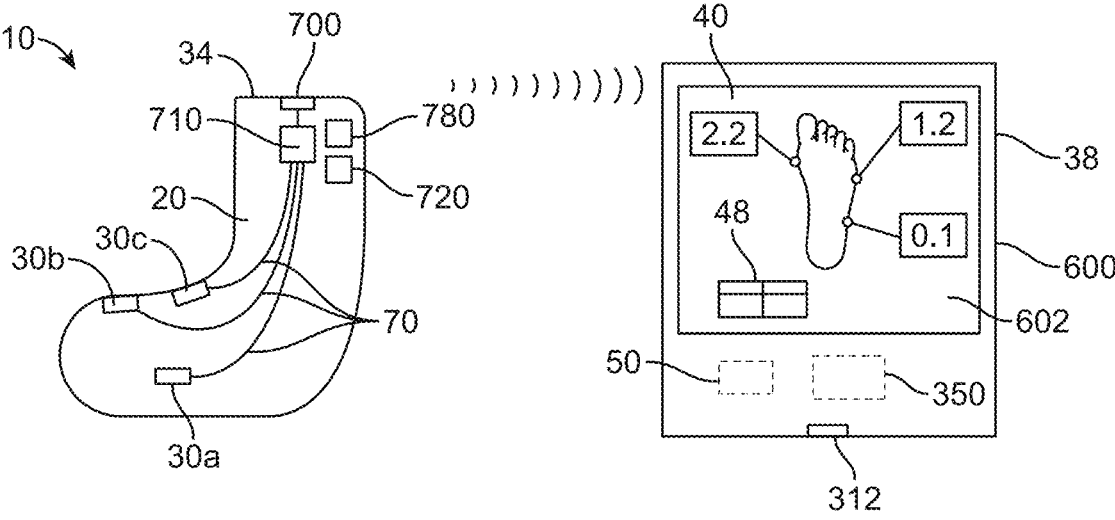
FIG. 8 illustrates another variation of the apparatus of FIG. 1.

In some cases, the wearable device 34 of the apparatus 10 may optionally also include a memory/register 780 configured to store data provided by the sensors 30*a*-30*c* (FIG. 8). The memory/register 780 may be configured to store the sensor data by themselves. Alternatively, the memory/register 38 may be configured to store the sensor data with their respective sensor identifiers. In some cases, the memory/register 780 may be configured to store the sensor data, their respective sensor identifiers, and also time data of the respective sensor data. The time data indicate the timing at which respective sensor data were generated. In some embodiments, the processing unit 710 is configured to package the sensor data, the sensor identifiers, and the time data, and transmit the packaged information for storing in the memory/register 780. The sensor data, the sensor identifiers, and the time data may be stored in the memory/register 780 using a data structure that associates these information with respect to each other.

The memory/register 780 is advantageous because it allows the wearable device 34 to be used by itself without the user interface device 38. In particular, the user may wear the wearable device 34 and may use it with a shoe to sample sensor values from the sensors 30. During the sampling phase, the wearable device 34 is not required to be coupled to or to communicate with the user interface device 38. Instead, the sensor values are stored in the memory/register 780. At a later time, the wearable device 34 may communicate with the user interface device 38 (e.g., via a pairing process). After the communication link between the wearable device 34 and the user interface device 38 is established via the pairing process, the processing unit 710 may then retrieve the stored sensor data and the sensor identifiers from the memory/register 780, and may then transmit them to the user interface device 38 via the wireless device 700. Upon receiving the sensor data and the sensor identifiers, the user interface device 38 displays the sensor data at the screen 602. The sensor identifiers allow the user interface device 38 to know the corresponding positions with respect to the foot/wearable device for which the respective sensor data were collected, and/or where to display the corresponding sensor data.

Figure 9:
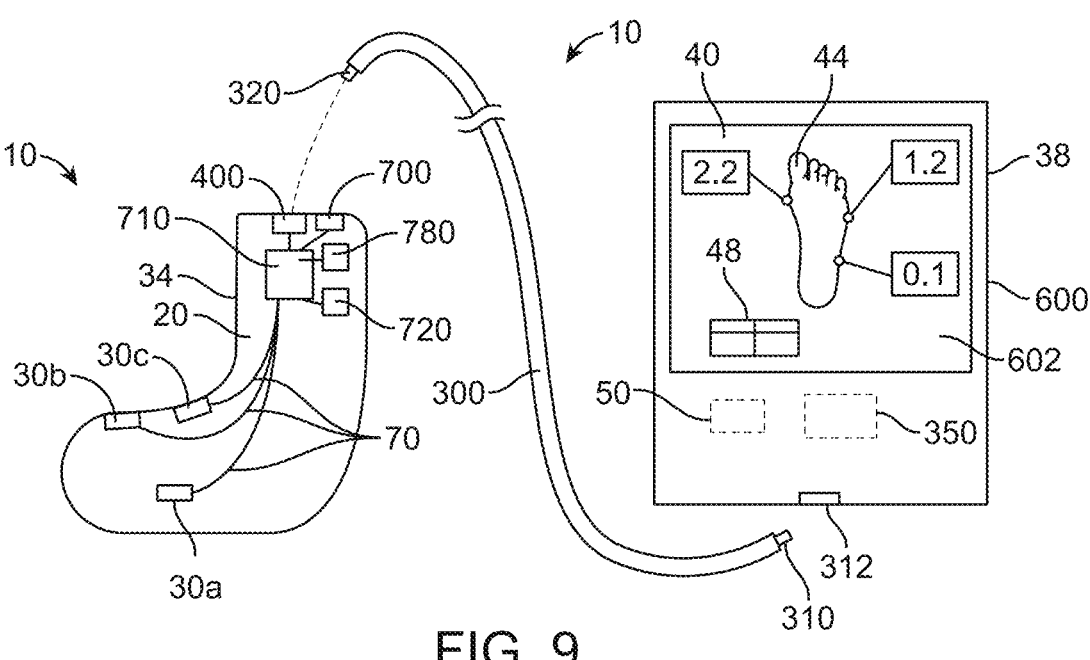
FIG. 9 illustrates another variation of the apparatus of FIG. 1.

As shown in FIG. 9, in some cases, the wearable device 34 may include both the wireless device 700 and the connector 400. This allows the wearable device 34 to communicate with the user interface device 38 using two alternative techniques—i.e., using the wireless device 700 to transmit the sensor data wirelessly, or using the cable 300 coupled to the connector 400 to transmit the sensor data.

Figure 10:
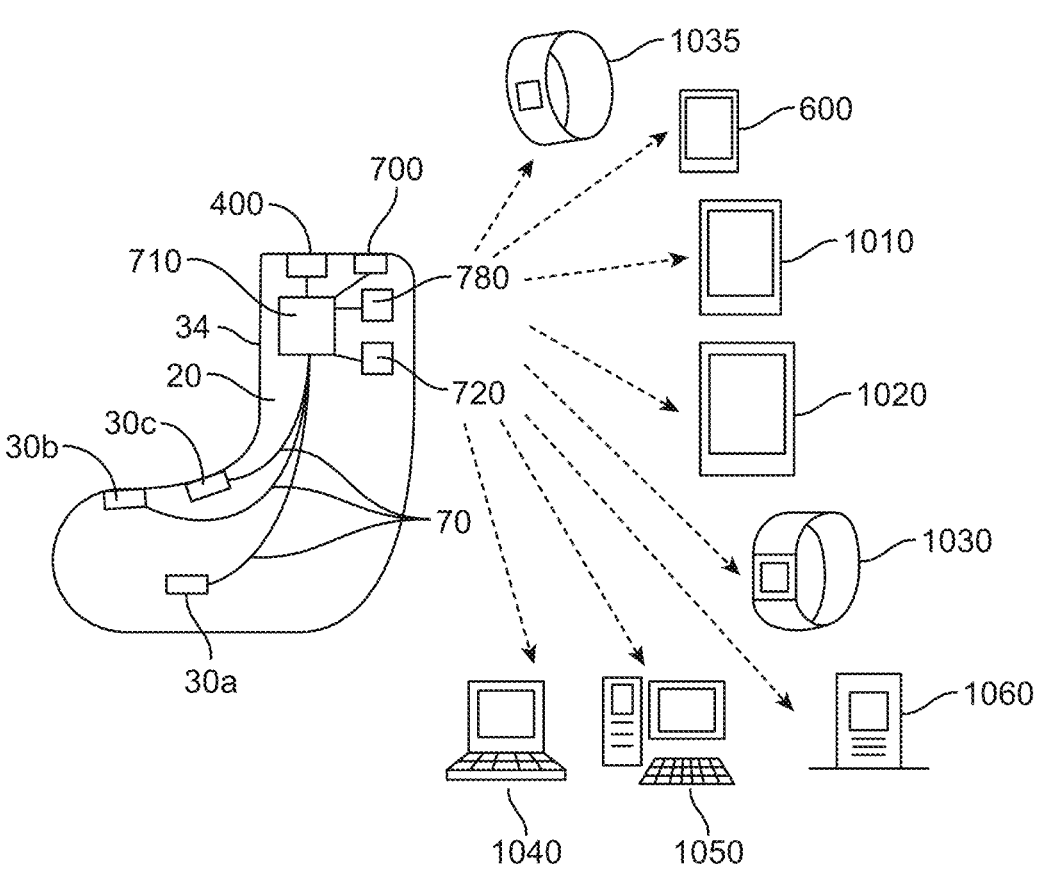
FIG. 10 illustrates another variation of the apparatus of FIG. 1.

Although the user interface device 38 has been described as a phone 600 in the above embodiments, in other embodiments, the user interface device 38 may be an iPad 1010, a tablet 1020, a watch 1030 (e.g., iWatch), a sport-band 1035, a laptop 1040, a computer 1050, a server 1060, or any of other devices that are capable of receiving and displaying data (FIG. 10). It should be noted that the wearable device 34 may transmit (e.g., via the wireless transmitter 700 or the cable 300) sensor data from the sensors 30 to any device that is away from the wearable device 34.

Figures 11A, 11B, 11C, 11D, 11E, 12A, 12B, 12C, 12D:
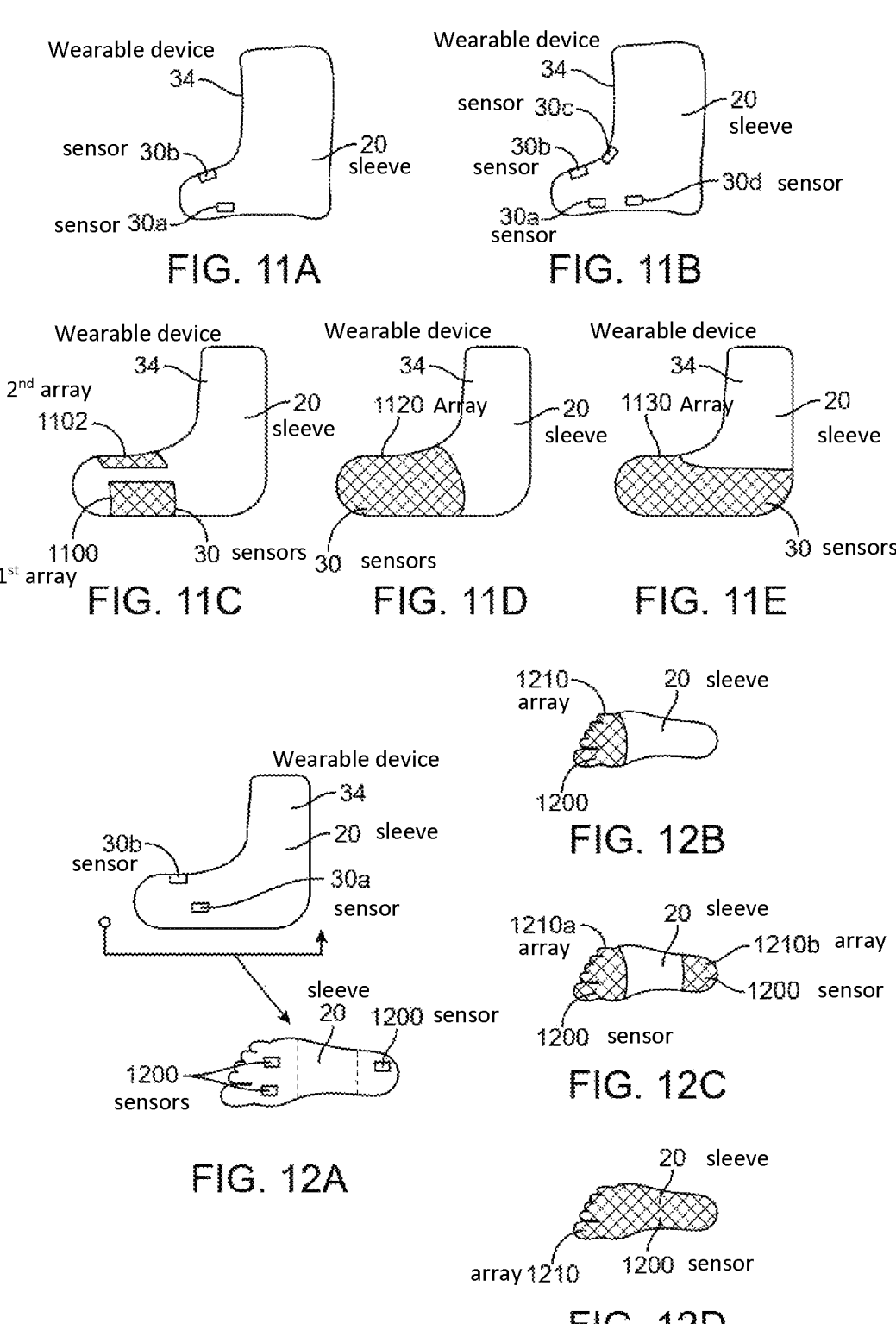

In the above embodiments, the wearable device 34 (in any of FIGS. 1-4 and 6-10) is described as having three sensors 30*a*-30*c*. In other embodiments, the wearable device 34 (in any of FIGS. 1-4 and 6-10) may have fewer than three sensors 30, such as two sensors 30*a*, 30*b* (FIG. 11A), or more than three sensors 30, such as four sensors 30*a*-30*d* (FIG. 11B). The sensors 30*a*, 30*d* are at respective locations with respect to the elastic sleeve 20 so that when the user wears the apparatus 10, the sensors 30*a*, 30*d* will be at a medial side of the foot. The sensors 30*b*, 30*c* are at respective locations with respect to the elastic sleeve 20 so that when the user wears the apparatus 10, the sensors 30*b*, 30*c* will be at a lateral side of the foot. The sensors 30*a*, 30*b* are closer to the front of the foot, while the sensors 30*c*, 30*d* are closer to the middle of the foot. Each of the sensors 30*a*-30*d* is configured to sense force, pressure, or a characteristic associated with force/pressure applied at the sensor 30.

In further embodiments, the wearable device 34 (in any of FIGS. 1-4 and 6-10) may have one or more arrays of sensors, with each sensor being configured to sense force, pressure, or a characteristic associated with force/pressure. For example, as shown in FIG. 11C, the wearable device 34 may include a first array 1100 of sensors 30, and a second array 1102 of sensors 30 in some embodiments. The first array 1100 of sensors 30 are at a first location with respect to the elastic sleeve 20 so that when the user wears the apparatus 10, the first array 1100 of sensors 30, or at least a majority of the sensors 30 in the first array 1100, will be at a medial side of the foot. The second array 1102 of sensors 30 are at a second location with respect to the elastic sleeve 20 so that when the user wears the apparatus 10, the second array 1102 of sensors 30, or at least a majority of the sensors 30 in the second array 1102, will be at a lateral side of the foot.

As another example, as shown in FIG. 11D, the wearable device 34 (in any of FIGS. 1-4 and 6-10) may include a single array 1120 of sensors 30 in other embodiments. The array 1120 of sensors 30 are disposed at the front of the elastic sleeve 20, and extends from the medial side of the foot, over the top of the foot, to the lateral side of the foot.

This configuration allows force, pressure, or a characteristic associated with force/pressure, to be sensed by sensors 30 at the medial side, the top, and the lateral side, of the foot.

FIG. 11E shows another example, in which the wearable device 34 (in any of FIGS. 1-4 and 6-10) may include a single array 1130 of sensors 30. The array 1130 of sensors 30 are disposed at the elastic sleeve 20, so that when the user wears the wearable device 34, the sensors 30 are circumferentially around the sides of the foot. Such configuration allows force, pressure, or a characteristic associated with force/pressure, to be sensed by sensors 30 around the foot of the user. In the illustrated example, the array 1130 of sensors 30 have multiple rows that are disposed circumferentially around the foot. In other embodiments, the array 1130 of sensors 30 may be a single row of sensors 30 disposed circumferentially around the foot when the user wears the wearable device 34.

In any of the embodiments described above (e.g., any of the embodiments of FIGS. 1-4 and 6-11), the wearable device 34 may optionally further include one or more sensors 1200 at a bottom of the elastic sleeve 20, such that when the user wears the wearable device 34, the sensor(s) 1200 will be at a bottom of the user's foot (FIG. 12A). The sensor 1200 at the bottom of the user's foot is advantageous because it can sense force/pressure to monitor and/or track an activity of the user. In one implementation, the force/pressure sensed by the sensor 1200 may be transmitted (wirelessly or through a cable) from the wearable device 34 to the user interface device 38 (e.g., via the wireless device 700 or the cable 300). For example, the processing unit 710 of the wearable device 34 may sample sensor data from the sensor(s) 1200, and the timing at which the sensor data are generated, and combine them to form a time series. The wearable device 34 then transmits the time series to the user interface device 38. The user interface device 38 is configured to analyze the time series, and determine an activity that the user is performing (e.g., whether the user is walking, running, jumping, etc.). In some cases, the user interface device 38 may determine activity metric(s) based on the time series. For example, the user interface device 38 may determine calories burn, number of steps, etc. The user interface device 38 may display the determined activity and/or the activity metric(s) via the screen 600.

In the embodiments of FIG. 12A, there are two sensors 1200 at respective locations with respect to the elastic sleeve 20 so that when the user wears the elastic sleeve 20, the sensors 1200 will be at a bottom of the foot distal to a lisfrank's joint. There is also a sensor 1200 at a location with respect to the elastic sleeve 20 so that when the use wears the elastic sleeve 20, the sensor 1200 will be at a bottom of the foot proximal to the chopart's joint.

In the illustrated example, the wearable device 34 has two sensors 1200 at the front of the elastic sleeve 20, and one sensor 1200 at the rear of the elastic sleeve 20. In other cases, the wearable device 34 may have more than two sensors 1200 at the front of the elastic sleeve 20, or a single sensor 1200 at the front of the elastic sleeve 20. For example, in some embodiments in which the wearable device 34 has two sensors 30 at respectively the medial and lateral side (first and second locations) of the elastic sleeve 20, the wearable device 34 may have a third sensor 1200 at a third location with respect to the elastic sleeve 20 so that when the user wears the wearable device 34, the third sensor 1200 will be at a bottom of the foot distal to a lisfrank's joint. The wearable device 34 may optionally also include a fourth sensor 1200 at a fourth location with respect to the elastic sleeve 20 so that when the user wears the wearable device 34, the fourth sensor 1200 will be at the bottom of the foot proximal to the chopart's joint. Also, in other cases, the wearable device 34 may have more than one sensor 1200 at the rear of the elastic sleeve 20.

FIG. 12B shows another example in which the wearable device 34 has an array 1210 of sensors 1200 at the bottom of the elastic sleeve 20. The array 1210 of sensors 1200 are configured to sense forces/pressures at the bottom of the foot of the user towards the front of the foot. In some cases, the wearable device 34 may further include another array of sensors 1200. As shown in FIG. 12C, the wearable device 34 may include a first array 1210a of sensors 1200, and a second array 1210b of sensors 1200. The first array 1210a of sensors 1200 is at a first location with respect to the elastic sleeve 20 so that when the user wears the apparatus 10, the first array 1210a of sensors 1200 will be at a front bottom of the foot. The second array 1210b of sensors 1200 is at a second location with respect to the elastic sleeve 20 so that when the user wears the apparatus 10, the second array 1210b of the sensors 1200 will be at a rear bottom of the foot.

FIG. 12D shows another example in which the wearable device 34 has a single array 1210 of sensors 1200 at the bottom of the elastic sleeve 20. The array 1210 of sensors 1200 extend from the front to the rear of the elastic sleeve 20.

In some embodiments, at least a part of the array 1210 of sensors 1200 is located with respect to the elastic sleeve 20 so that when the user wears the elastic sleeve 20, the at least the part of the array 1210a of sensors 1200 is below a metatarsal head of the foot, a tibial sesamoid of the foot, a fibular sesamoid of the foot, a great toe of the foot, a plantar medial tubercle of the foot, a calcaneal-cuboid joint of the foot, a 5th metatarsal base of the foot, or any combination of the foregoing.

In the above embodiments, the user interface device 38 has been described as having the comfort-level chart 48. The comfort-level chart 48 may be presented to the user or caregiver for viewing. In other embodiments, the user interface device 38 may not provide or display the comfort-level chart 48. Instead, the comfort-level chart 48 (i.e., information of the comfort-level chart 48) may be stored in a non-transitory medium. In such cases, during use, the processing unit 350 of the user interface device 38 may be configured to access the comfort-level chart 48, and may determine comfort levels for the various respective pressure-sensing areas at the wearable device based on sensor values. For example, the processing unit 350 may determine that the first sensor value of "2.2 V" is within the range of values that corresponds with "uncomfortable" level according to the comfort-level chart 48. The processing unit 350 may then generate a signal to inform the user that the force/pressure at the corresponding area of the foot is too high or "uncomfortable". Thus, as used in this specification, the term "comfort-level chart" is not limited to a displayed item or object, and may alternatively refer to information (i.e., mapping information mapping metric values to respective comfort levels, or threshold(s) for identifying comfort levels, etc.) stored in a non-transitory medium for access by the processing unit 350.

Figure 13:
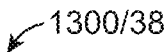
FIG. 13 illustrates a user interface device in accordance with some embodiments.
Figure 13:
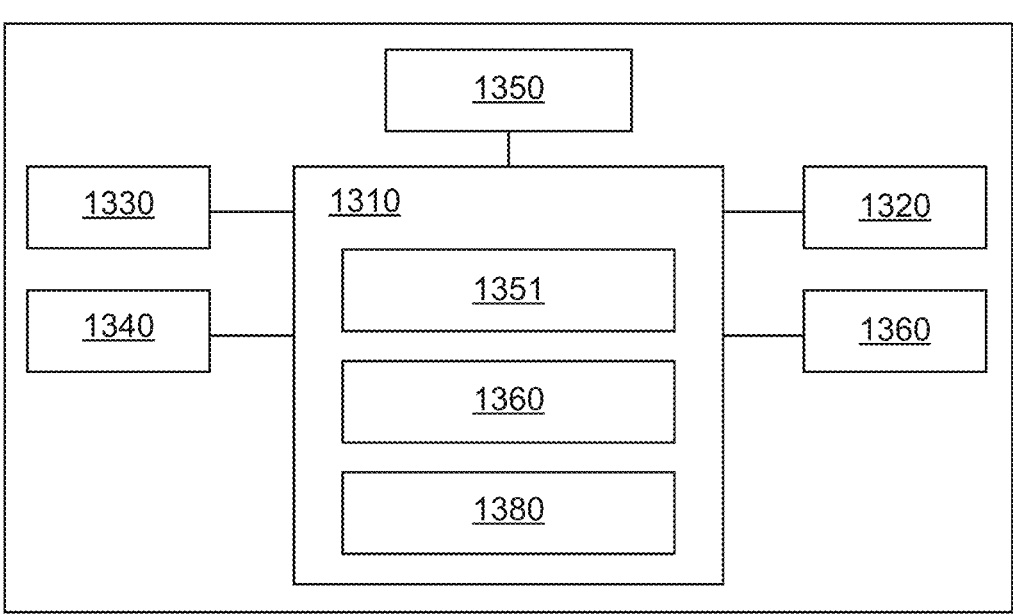

FIG. 13 illustrates an example of a user interface device 1300. The user interface device 1300 may be any of the user interface devices 38 described herein (such as any of the interface devices 38 described with reference to FIGS. 1-4, and 6-10). The user interface device 1300 includes a processing unit 1310, a memory (non-transitory medium) 1320, a screen 1330, and a communication device 1340. The user interface device 1300 also includes a port 1350 configured to couple with a cable (e.g., the cable 300), and a battery 1360. The communication device 1340 of the user interface device 1300 is configured to communicate wirelessly with the communication device 700 of the wearable device 34 (in the embodiments in which the wearable device 34 includes the communication device 700). In particular, the user interface device 1300 may include a pairing module 1351 configured to perform a pairing process to establish a wireless link with the wearable device 34 (e.g., sock) via the respective communication devices 1340, 700. For example, the pairing module 1351 may be configured to receive a wearable device ID transmitted wirelessly from the wearable device 34, and check to see if the wearable device ID is a "trusted" device/a device that was previously connected with the user interface device 1300. If so, the pairing module 1351 then establishes the wireless link. After the wireless link is established, the wireless device 1340 of the user interface device 1300 may then wirelessly receive sensor signals from the sensors 30 transmitted by the wireless device 700 of the wearable device 34 (e.g., sock).

The processing unit 1310 is configured to process the sensor signals. In some embodiments, the processing unit 1310 may pass the sensor signals for storage in the memory 1320. In some cases, the processing unit 1310 may reformat the sensor signals before storing them in the memory 1320. Also, in some cases, the processing unit 1310 may determine a metric value based on each sensor signal, and may store the metric value in the memory 1320. For example, the processing unit 1310 may calculate a force value or a pressure value based on the sensor signal, or may access a lookup table that maps sensor values to force/pressure values to determine the force/pressure values.

Also, in some cases, the processing unit 1310 may process the sensor signals, and may include a graphics generator 352 configured to generate output based on the processed sensor signals. The output may be a graphical output for display by the screen 1330. In some embodiments, graphics generator 1352 of the processing unit 1310 is configured to retrieve a foot diagram (e.g., foot diagram 44) from the memory 1320, and operates the screen 1330 to display the foot diagram 44 at the screen 1330. The graphics generator 1352 of the processing unit 1310 is also configured to cause the screen 1330 to display graphics indicating amounts of force/pressure sensed by the sensors 30 at different locations of the user's foot. For examples, the graphics may be numerical values of the sensor values, colored objects (e.g., red object representing discomfort, green object representing comfort, etc.), etc. In some embodiments, the graphics may be a heat map superimposed over the foot diagram 44, wherein the heat map is color-coded so that different colors representing different amounts of force/pressure at the user's foot.

In some embodiments, the processing unit 1310 includes a comparator 1360 configured to compare each sensor value with a first threshold. If the sensor value is below the first threshold, then the processing unit 1310 may determine that the area (corresponding with the sensor value) at the user's foot is "comfortable". In some cases, the first threshold may be the upper limit of a range of metric values considered to be "comfortable". For example, the first threshold may be 1.87V, which corresponds with the upper limit of the range 0-1.87V described previously with reference to the comfort-level chart 48. Also, if the sensor value is above the first threshold, or a second threshold, then the processing unit 1310 may determine that the area (corresponding with the sensor value) at the user's foot is "uncomfortable". In some cases, the second threshold may be equal to or higher than the first threshold. For example, the second threshold may be 1.87V, which corresponds with the lower limit of the range>1.87V described previously with reference to the comfort-level chart 48. Thus, in some embodiments, information in the comfort-level chart 48 may be stored in the memory 1320 to implement one or more thresholds for use by the comparator 1360 of the processing unit 1310.

In some embodiments, the graphics generator 1352 may generate graphics for presentation by the screen 1330 to indicate whether a sensor output is too high (indicating discomfort) and/or whether a sensor output is within a normal range (indicating comfort). For example, the graphics generator 1352 may generate a red object for display by the screen 1330 if the sensor output is determined by the comparator 1360 as too high, and/or may generate a green object for display by the screen 1330 if the sensor output is determined by the comparator 1360 as within the normal range. The color objects may be displayed with respect to the foot diagram 44 so that the user or the caregiver can see which part(s) of the user's foot has high pressure point(s) and/or normal pressure point(s). Alternatively or additionally, the graphics generator 1352 may generate other forms of graphics in other embodiments. For example, the graphics generator 1352 may display sensor values with respect to foot diagram 44, and may highlight the sensor value that is considered too high by the comparator 1360. The highlighting of the sensor value may be a blinking value, a value displayed in a different color, a value with a higher image intensity, a value with a marker displayed next to it, etc.

In some embodiments, the processing unit 1310 may optionally further include a recommendation generator 1380 configured to provide a recommendation regarding a size of a shoes for the user. In one implementation, based on the sensor signals generated by the sensors 30, the processing unit 1310 determines whether a sensed force/pressure is too high (e.g., metric value exceeding a threshold). If so, the processing unit 1310 may then recommend a new shoe size for the user.

One or more components of the processing unit 1310 may be implemented using hardware, software, or a combination of both. For example, in some cases, the processing unit 1310 may include a software (e.g., application) that provides the functionalities of the pairing module 1351, the graphics generator 1352, the comparator 1360, and the recommendation generator 1380. In such cases, the software may be considered as comprising the pairing module 1351, the graphics generator 1352, the comparator 1360, and the recommendation generator 1380. The software may be downloaded from a server to the user interface device 1300.

In the above embodiments, the sensors 30 are described as being coupled to the elastic sleeve 20 (e.g., sock). The coupling may be permanent or non-permanent. For example, the sensors 30 may be permanently coupled to the elastic sleeve 20 via adhesive and/or stitching. As another example, the sensors 30 may be non-permanently coupled to the elastic sleeve 20 via a connector that allows the sensors 30 to be detachably coupled to the elastic sleeve 20. This feature is advantageous because it allows the elastic sleeve 20 to be washed or be replaced with another elastic sleeve 20.

Figure 14:
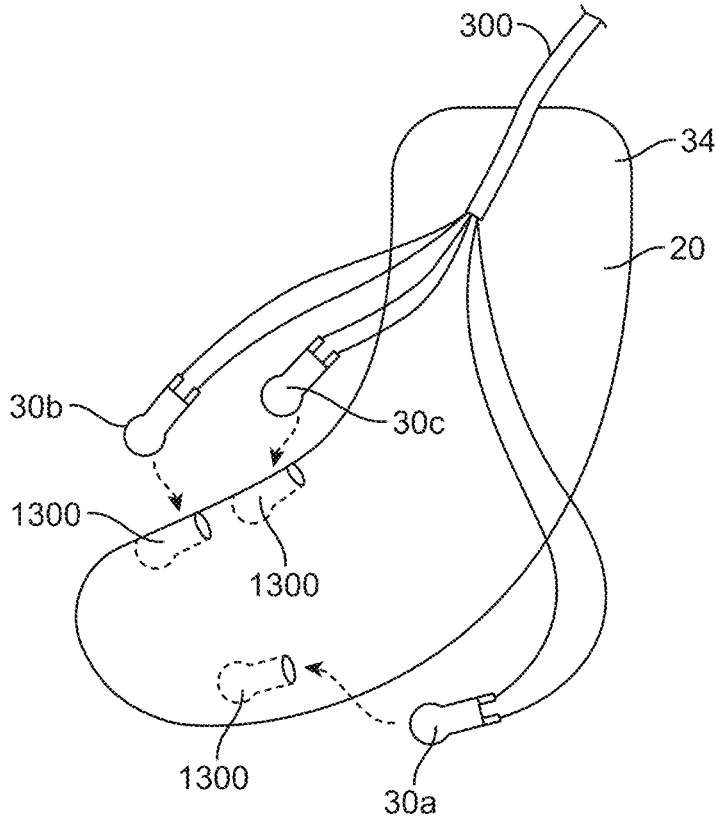
FIG. 14 illustrates a variation of the wearable device of FIG. 1.

Also, in some embodiments, the elastic sleeve 20 may include one or more pockets 1300 configured (e.g., sized and/or shaped) to house respectively one or more sensors 30 (FIG. 14). In such cases, each sensor 30 with the wires attached may be inserted into the pocket of the elastic sleeve 20. The pocket may have an opening with a width that is smaller than a maximum cross-sectional width of the cavity holding the sensor 30. The opening may be stretched to allow the sensor 30 to be inserted into the cavity of the pocket, and will prevent, or will at least provide some resistance against the sensor 30 being dislodged from the pocket. The pocket feature is advantageous because it allows the elastic sleeve 20 to be washed or be replaced with another elastic sleeve 20.

In some embodiments, the wearable device 34 may be provided in different sizes and/or colors. For example, the wearable device 34 may be made to be in sizes XS, S, M, L, XL. As another example, the wearable device 34 may be made to be in infant size, toddler size, teenage size, and adult size. Also, in some cases, for each size, the wearable device 34 may be made to be available in different colors (e.g., black, white, pink, blue, grey, red, etc.).

Specialized Processing System

Figure 15:
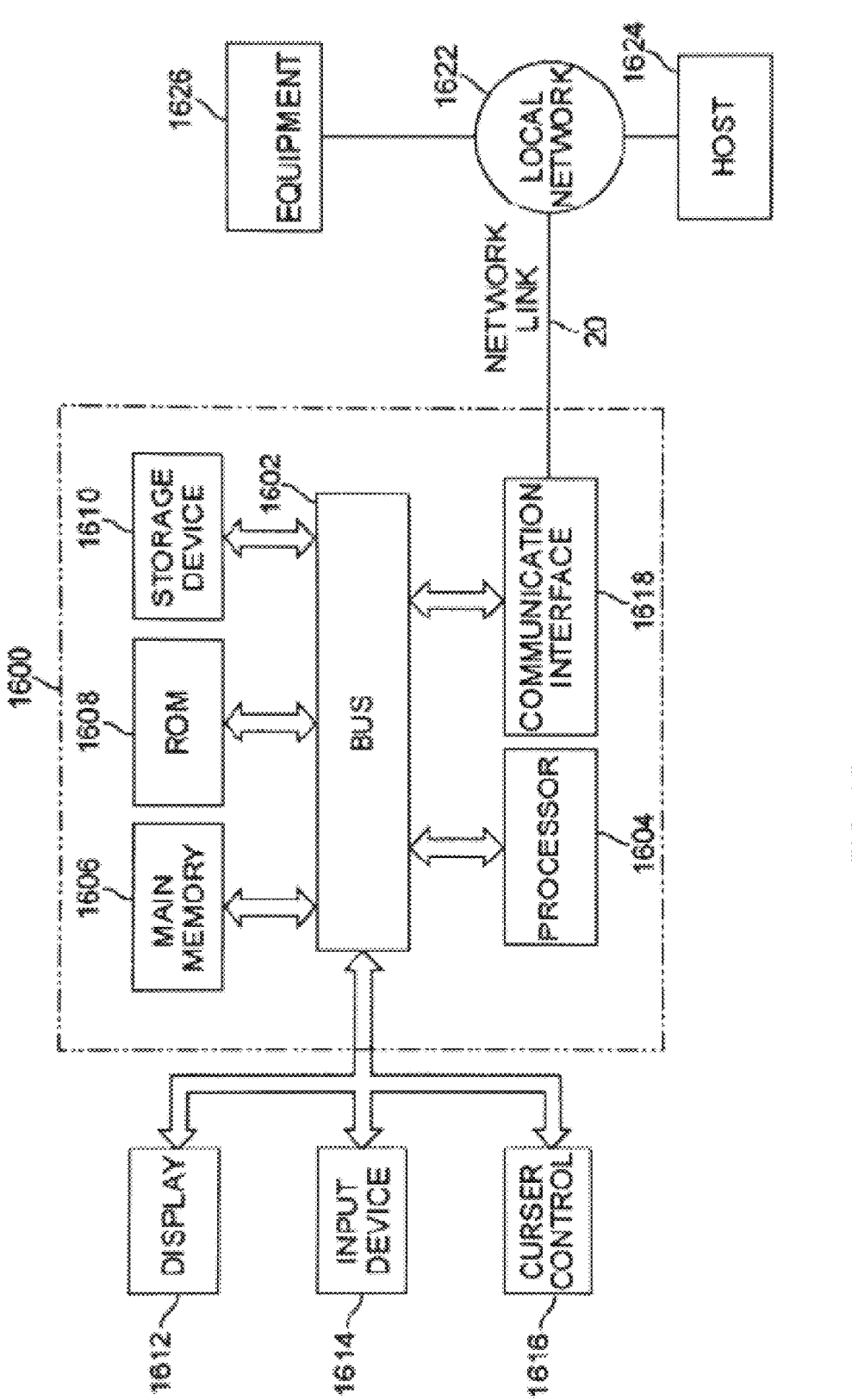
FIG. 15 illustrates a specialized processing system in accordance with some embodiments.

FIG. 15 illustrates a specialized processing system 1600 in accordance with some embodiments. The processing system 1600 may implement one or more processing units of the apparatus 10. For example, the processing system 1600 may implement the processing unit 710/1310 of the wearable device 34, and/or the processing unit 530 of the user interface device 38.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 1612, such as a screen or a flat panel, for displaying information to a user. An input device 1614, including alphanumeric and other keys, or a touchscreen, and/or any of other data capture devices (sensors), is coupled to the bus 1602 for communicating information and command selections to processor 1604. Another type of user input device is cursor control 1616, such as a 2D touchpad, a touchscreen, a trackball, or cursor direction keys for communicating direction information and command selections to processor 1604 and/or for controlling cursor movement on display 1612. This input device typically has two degrees of freedom in two axes, a first axis (e.g., x) and a second axis (e.g., y), that allows the device to specify positions in a plane. The input device 1614 and/or the cursor control device 1616 may be the same device in some embodiments. Also, the input device 1614 and/or the cursor control device 1616 may be any 2D input device or 3D input device.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, SD disks, such as the storage device 1610. A non-volatile medium may be considered an example of non-transitory medium. Volatile media includes dynamic memory, such as the main memory 1606. A volatile medium may be considered an example of non-transitory medium. Transmission media includes cables, wire and fiber optics, including the wires that comprise the bus 1602. Transmission media can also take the form of acoustic or light waves, such as those generated during radio wave and infrared data communications.

Common forms of processor-readable media include, for example, hard disk, a magnetic medium, a CD-ROM, any other optical medium, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a storage of a remote computer or remote device. The remote computer or device can send the instructions over a network, such as the Internet. A receiving unit local to the processing system 1600 can receive the data from the network, and provide the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card to provide a data communication. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Also, as used in this specification, the term "signal" may refer to one or more signals. By means of non-limiting examples, a signal may include one or more data, one or more information, one or more signal values, one or more discrete values, etc.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

What is claimed:

1. A method of determining compression at a foot of a user, the method comprising:

providing an apparatus comprising an elastic sleeve to be worn at the foot of the user, and a plurality of sensors coupled to the elastic sleeve, the sensors comprising a first sensor and a second sensor;

wherein when the user wears the apparatus, the first sensor is (1) facing a first peripheral side of the foot, (2) below an ankle of the user, (3) away from a bottom of the foot, and (4) away from a top of the foot;

wherein when the user wears the apparatus, the second sensor is (1) facing a second peripheral side of the foot, (2) below the ankle of the user, (3) away from the bottom of the foot, and (4) away from the top of the foot;

wherein the method further comprises an act of sensing, by the first sensor, a characteristic indicative of a first force or a first pressure;

wherein the plurality of sensors also comprises a third sensor, and wherein when the user wears the apparatus, the third sensor is facing the bottom of the foot distal to a lisfrank of a joint of the user; and wherein the plurality of sensors also comprises a fourth sensor, and wherein when the user wears the apparatus, the fourth sensor is facing the bottom of the foot proximal to a chopart of the joint of the user.

2. The method of claim 1, wherein the elastic sleeve is a sock comprising a first electrically non-conductive layer and a second electrically non-conductive layer, and wherein the sensors are disposed between the first non-conductive layer of the sock and the second non-conductive layer of the sock.

3. The method of claim 1, wherein the sensors further comprise an array of sensors, wherein when the user wears the apparatus, the array of sensors is at the bottom of the foot.

4. The method of claim 1, wherein the apparatus further comprises one or more transmitters, and wherein the method further comprises transmitting sensor data from the sensors to a device away from the apparatus.

5. The method of claim 4, wherein the device comprises a cellular phone, an iPad, a tablet, a computer, a sport-band, a watch, or a server.

6. The method of claim 1, wherein the apparatus further comprises a battery compartment configured to house a battery, and wherein the sensors are configured to operate utilizing power from the battery.

7. The method of claim 1, wherein the apparatus further comprises an energy harvester configured to obtain energy from motion of the user.

8. The method of claim 1, wherein the apparatus further comprises an array of sensors, and wherein when the user wears the apparatus, at least a part of the array of sensors is below a metatarsal head of the foot, a tibial sesamoid of the foot, a fibular sesamoid of the foot, a great toe of the foot, a plantar medial tubercle of the foot, a calcaneal-cuboid joint of the foot, a 5th metatarsal base of the foot, or any combination.

9. The method of claim 1, wherein the apparatus further comprises one or more registers or one or more memories, and wherein the method further comprises storing, by the one or more registers or the one or more memories, sensor data from the sensors.

10. The method of claim 1, wherein the apparatus further comprises one or more displays, and wherein the method further comprises displaying information derived from sensor data provided by the plurality of sensors.

11. The method of claim 1, further comprising providing sensor data from the plurality of sensors in a data structure that correlates the sensor data with respective time points.

12. The method of claim 1, wherein the apparatus further comprises a mapping table in display form for viewing by the user, the mapping table mapping a first range of sensor values to a comfort classification, and mapping a second range of the sensor values to a discomfort classification, wherein the first range of the sensor values and the second range of the sensor values are pre-determined before the user uses the apparatus, and wherein the mapping table is configured to assist the user in determining whether a location at the foot of the user is having comfort or discomfort.

13. The method of claim 1, wherein the apparatus comprises a visual indicator, and wherein the method further comprises providing a visual indication by the visual indicator when a sensor value associated with the first sensor or the second sensor is above a threshold.

14. The method of claim 1, wherein the elastic sleeve is a sock, and wherein the apparatus further comprises a wireless device coupled to the sock, the wireless device configured to wirelessly transmit data based on output from the first sensor for reception by a handheld device.

15. The method of claim 1, wherein a vertical axis extending through the first sensor is away from the foot of the user when the user wears the apparatus.

16. The method of claim 1, wherein the elastic sleeve is a sock with an end having a sock opening, wherein the apparatus further comprises a cable extending from the end of the sock, and wherein the cable comprises wires respectively coupled to the first sensor and the second sensor.

17. The method of claim 1, further comprising; obtaining sensor outputs from the third sensor, and analyzing the sensor outputs to identify an activity performed by the user.

18. The method of claim 1, wherein the act of sensing is performed by the first sensor while the user is standing.

* * * * *